United States Patent
Ward

(10) Patent No.: US 10,144,838 B2
(45) Date of Patent: Dec. 4, 2018

(54) PRINTING INK

(71) Applicant: FujiFilm Speciality Ink Systems Limited, Broadstairs Kent (GB)

(72) Inventor: Jeremy Ward, Broadstairs Kent (GB)

(73) Assignee: Fujifilm Speciality Ink Systems Limited (GB)

( * ) Notice: Subject to any disclaimer, the term of this patent is extended or adjusted under 35 U.S.C. 154(b) by 0 days.

(21) Appl. No.: 15/578,909

(22) PCT Filed: Jun. 2, 2016

(86) PCT No.: PCT/GB2016/051620
§ 371 (c)(1),
(2) Date: Dec. 1, 2017

(87) PCT Pub. No.: WO2016/193728
PCT Pub. Date: Dec. 8, 2016

(65) Prior Publication Data
US 2018/0163066 A1 Jun. 14, 2018

(30) Foreign Application Priority Data
Jun. 2, 2015 (GB) .................................. 1509501.1

(51) Int. Cl.
| | |
|---|---|
| *C08F 20/56* | (2006.01) |
| *C09D 11/106* | (2014.01) |
| *C09D 11/101* | (2014.01) |
| *C09D 11/102* | (2014.01) |
| *C09D 11/322* | (2014.01) |
| *C07D 223/10* | (2006.01) |
| *C08F 20/18* | (2006.01) |
| *C08L 23/12* | (2006.01) |
| *C08L 27/04* | (2006.01) |

(52) U.S. Cl.
CPC .......... *C09D 11/106* (2013.01); *C07D 223/10* (2013.01); *C08F 20/18* (2013.01); *C08F 20/56* (2013.01); *C08L 23/12* (2013.01); *C08L 27/04* (2013.01); *C09D 11/101* (2013.01); *C09D 11/102* (2013.01); *C09D 11/322* (2013.01)

(58) Field of Classification Search
CPC ........ C07D 223/10; C08F 20/18; C08F 20/56; C08L 23/12; C08L 27/04; C09D 11/101; C09D 11/102; C09D 11/322
See application file for complete search history.

(56) References Cited

U.S. PATENT DOCUMENTS

| | | | |
|---|---|---|---|
| 9,546,255 | B2 | 1/2017 | Kawamura |
| 2016/0200635 | A1 | 7/2016 | Nouaille et al. |

FOREIGN PATENT DOCUMENTS

| | | |
|---|---|---|
| EP | 2 088 175 A1 | 8/2009 |
| EP | 2 371 910 A1 | 10/2011 |
| EP | 2 543 707 A1 | 1/2013 |
| JP | 2014 055210 A | 3/2014 |
| WO | 2006/035679 A1 | 4/2006 |
| WO | 2014/051702 A1 | 4/2014 |
| WO | 2014/155976 A1 | 10/2014 |

OTHER PUBLICATIONS

International Search Report and Written Opinion for corresponding application No. PCT/GB2016/051620 dated Aug. 16, 2016.
GB Search Report for priority application No. GB1509501.1 dated Nov. 5, 2015.

*Primary Examiner* — Lamson Nguyen
(74) *Attorney, Agent, or Firm* — Wood, Phillips, Katz, Clark & Mortimer

(57) ABSTRACT

The invention relates to an inkjet ink comprising: one or more monofunctional (meth)acrylate monomers, including 2-methyl-2-ethyl-1,3-dioxolane-4-yl)methyl acrylate (MEDA); a pigment; and a photoinitiator.

15 Claims, No Drawings

PRINTING INK

FIELD OF THE INVENTION

This invention relates to a printing ink and in particular to an inkjet ink that is suitable for printing onto a range of substrates.

BACKGROUND OF THE INVENTION

Radiation-curable inkjet inks contain radiation-curable material, such as radiation-curable monomers, which polymerise by irradiation with actinic radiation (usually ultraviolet light) in the presence of a photoinitiator. In inkjet printing, the inks must flow rapidly through the printing heads and hence they must have a low viscosity when jetted. The inks must also be resistant to drying or crusting in the reservoirs or nozzles. This places particular demands on the ink formulator, who also has to balance the requirements of the particular technical application, including adhesion to the substrate, flexibility, durability and the aesthetic quality of the final image.

Tetrahydrofurfuryl acrylate (THFA) is often used to provide good adhesion to variety of substrates, as well as producing a flexible film which is less liable to cracking and delamination. A further advantage of THFA is that it can solubilise chlorinated polyolefins, which in turn provides good adhesion to polyolefin substrates.

However, THFA is a hazardous monomer and bears the GHS hazard statement H314 (Causes severe skin burns and eye damage). There is also growing evidence that it may damage fertility or the unborn child. Thus, there is an urgent need in the art to move away from THFA.

BRIEF SUMMARY OF THE INVENTION

Accordingly, the present invention provides an inkjet ink comprising: one or more monofunctional (meth)acrylate monomers, including 2-methyl-2-ethyl-1,3-dioxolane-4-yl) methyl acrylate (MEDA); a pigment; and a photoinitiator.

The present invention provides an ink which offers the benefits of THFA-containing inks, without the associated hazards associated with this monomer.

DETAILED DESCRIPTION OF THE INVENTION

The ink of the present invention is a radiation-curable inkjet ink (often termed a "UV ink") and hence contains a radiation-curable diluent. By "radiation-curable" is meant a material that polymerises or crosslinks when exposed to actinic radiation, commonly ultraviolet light, in the presence of a photoinitiator. The diluent is based on monomers which provide the liquid phase for the ink prior to curing.

The ink contains one or more monofunctional (meth) acrylate monomers. The one or more monofunctional (meth) acrylate monomers includes 2-methyl-2-ethyl-1,3-dioxolane-4-yl)methyl acrylate (referred to herein as "MEDA"). MEDA has the formula:

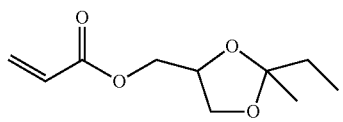

MEDA has been allocated CAS no. 69701-99-1, and is sometimes named alternatively as (2-methyl-2-ethyl-1,3-dioxoran-4-yl) methyl acrylate.

The ink may contain other monofunctional (meth)acrylate monomers, and in a preferred embodiment, the ink contains at least two monofunctional monomers (meth)acrylate monomers, including MEDA. Suitable monofunctional (meth)acrylate monomers which may additionally be present are selected from isobornyl acrylate (IBOA), phenoxyethyl acrylate (PEA), cyclic TMP formal acrylate (CTFA), 2-(2-ethoxyethoxy)ethyl acrylate, octa/decyl acrylate (ODA), tridecyl acrylate (TDA), isodecyl acrylate (IDA) and lauryl acrylate. IBOA is particularly preferred.

The MEDA is preferably present at 10-45% by weight, based on the total weight of the ink. The ink typically contains 10-70% by weight of monofunctional (meth)acrylate monomer, including MEDA, based on the total weight of the ink.

MEDA is provided as a replacement for THFA in inks which would otherwise require the presence of THFA. The ink will still function in the presence of tetrahydrofurfuryl acrylate (THFA), in terms of its printing and curing properties. However, to avoid the hazardous nature of THFA, the ink is preferably substantially free of THFA. The ink preferably contains less than 5% by weight, more preferably less than 2% by weight, more preferably less than 1% by weight and most preferably 0% of THFA, based on the total weight of the ink.

The ink may further include at least one N-vinyl amide monomer and/or N-(meth)acryloyl amine. N-Vinyl amides are well-known monomers in the art. N-Vinyl amides have a vinyl group attached to the nitrogen atom of an amide which may be further substituted in an analogous manner to the (meth)acrylate monomers. Preferred examples are N-vinyl caprolactam (NVC) and N-vinyl pyrrolidone (NVP). Similarly, N-acryloyl amines are also well-known in the art. N-Acryloyl amines also have a vinyl group attached to an amide but via the carbonyl carbon atom and again may be further substituted in an analogous manner to the (meth) acrylate monomers. A preferred example is N-acryloylmorpholine (ACMO). N-Vinyl amides are particularly preferred, and most preferably NVC.

The ink typically contains 10-30% by weight of N-vinyl amide and/or N-(meth)acryloyl amine monomers, based on the total weight of the inkjet ink.

A particularly preferred monofunctional monomer combination for the present invention is MEDA, IBOA and NVC. More preferably, MEDA, IBOA and NVC are the sole monofunctional monomers present in the ink.

The ink may further comprise one or more di- and/or multifunctional monomer, such as a di-/multifunctional (meth)acrylate monomer or a di-/multifunctional vinyl ether.

Examples of the di-/multifunctional acrylate monomers include hexanediol diacrylate (HDDA), trimethylolpropane triacrylate, pentaerythritol triacrylate, polyethyleneglycol diacrylate, for example, tetraethyleneglycol diacrylate), dipropyleneglycol diacrylate, tri(propylene glycol) triacrylate, neopentylglycol diacrylate, bis(pentaerythritol) hexaacrylate, and the acrylate esters of ethoxylated or propoxylated glycols and polyols, for example, propoxylated neopentyl glycol diacrylate, ethoxylated trimethylolpropane triacrylate, and mixtures thereof. In addition, multifunctional acrylate monomers include esters of methacrylic acid (i.e. methacrylates), such as hexanediol dimethacrylate, trimethylolpropane trimethacrylate, triethyleneglycol dimethacrylate, diethyleneglycol dimethacrylate, ethyleneglycol dimethacrylate, 1,4-butanediol dimethacrylate, and mixtures thereof. Difunctional (meth)acrylate monomers are particularly preferred, and most preferably HDDA.

The term "(meth)acrylate" is intended herein to have its standard meaning, i.e. acrylate and/or methacrylate. Mono and multifunctional are also intended to have their standard meanings, i.e. one and two or more groups, respectively, which take part in the polymerisation reaction on curing.

A particularly preferred monomer combination for the present invention is MEDA, IBOA, NVC and HDDA. More preferably, MEDA, IBOA, NVC and HDDA are the sole monomers present in the ink.

The ink may comprise a radiation-curable (i.e. polymerisable) oligomer, such as a (meth)acrylate oligomer. Any radiation-curable oligomer that is compatible with the other ink components is suitable for use in the ink.

The term "curable oligomer" has its standard meaning in the art, namely that the component is partially reacted to form a pre-polymer having a plurality of repeating monomer units, which is capable of further polymerisation. The oligomer preferably has a molecular weight of at least 600. The molecular weight is preferably 4,000 or less. Molecular weights (number average) can be calculated if the structure of the oligomer is known or molecular weights can be measured using gel permeation chromatography using polystyrene standards.

The oligomers may possess different degrees of functionality, and a mixture including combinations of mono, di, tri and higher functionality oligomers may be used. The degree of functionality of the oligomer determines the degree of crosslinking and hence the properties of the cured ink. The oligomer is preferably multifunctional meaning that it contains on average more than one reactive functional group per molecule. The average degree of functionality is preferably from 2 to 6.

Radiation-curable oligomers comprise a backbone, for example a polyester, urethane, epoxy or polyether backbone, and one or more radiation-curable groups. The oligomer preferably comprises a urethane backbone. The polymerisable group can be any group that is capable of polymerising upon exposure to radiation. Preferably the oligomers are (meth)acrylate oligomers.

Particularly preferred radiation-curable oligomers are urethane acrylate oligomers as these have excellent adhesion and elongation properties. Most preferred are di-, tri-, tetra-, penta- or hexa-functional urethane acrylates.

The amount of radiation-curable oligomer, when present, is 0.1-10% by weight, based on the total weight of the ink.

The ink may also contain a resin. The resin preferably has a weight-average molecular weight (Mw) of 10-50 KDa, and most preferably 15-35 KDa. The Mw may be measured by known techniques in the art, such as gel permeation chromatography (GPC), using a polystyrene standard. The resin preferably has a viscosity of 5-200 mPas at 25° C. It is preferably soluble in the liquid medium of the ink (the radiation-curable diluent and, when present, additionally the solvent).

The resin is a passive (i.e. inert) resin, in the sense that it is not radiation curable and hence does not undergo crosslinking under the curing conditions to which the ink is subjected.

The resin is preferably a chlorinated polyolefin, e.g. a chlorinated polyethylene, chlorinated polypropylene, or mixtures or copolymers thereof. The chlorine content is preferably 10-40% by weight, more preferably 18-23% by weight, based on the total weight of the chlorinated polyolefin. Such materials are commercially available, e.g. as CP343-1 from Eastman Chemical Co.

The resin may improve adhesion of the ink to the substrate. It is preferably soluble in the ink. The resin is preferably present at 0.1-5% by weight, based on the total weight of the ink.

The ink of the present invention also includes a photoinitiator which under irradiation, for example using ultraviolet light, initiates the polymerisation of the radiation-curable diluent. Preferred are photoinitiators which produce free radicals on irradiation (free radical photoinitiators) such as, for example, benzophenone, 1-hydroxycyclohexyl phenyl ketone, 2-benzyl-2-dimethylamino-(4-morpholinophenyl) butan-1-one, benzil dimethylketal, bis(2,6-dimethylbenzoyl)-2,4,4-trimethylpentylphosphine oxide or mixtures thereof. Such photoinitiators are known and commercially available such as, for example, under the trade names Irgacure, Darocur (from Ciba) and Lucerin (from BASF). The ink of the present invention is preferably cured by ultraviolet irradiation. In a preferred embodiment the radiation-curable material polymerises by free-radical polymerisation.

Preferably the photoinitiator is present from 1 to 20% by weight, preferably from 5 to 15% by weight, of the ink.

The ink-jet ink of the present invention also includes a pigment dispersed in the liquid medium of the ink. Dispersible pigments are known in the art and commercially available such as, for example, under the trade-names Paliotol (available from BASF plc), Cinquasia, Irgalite (both available from Ciba Speciality Chemicals) and Hostaperm (available from Clariant UK). The pigment may be of any desired colour such as, for example, Pigment Yellow 13, Pigment Yellow 83, Pigment Red 9, Pigment Red 184, Pigment Blue 15:3, Pigment Green 7, Pigment Violet 19, Pigment Black 7. Especially useful are black and the colours required for trichromatic process printing. The ink of the present invention works particularly well with cyan and black pigments in providing good adhesion of the ink to the substrate. In a preferred embodiment, the pigment is a cyan or black pigment. Mixtures of pigments may be used. Often, pigments are commercially available as dispersions. If the dispersion contains a monofunctional monomer, it should be taken into account when assessing the amounts of the monomers present.

The total proportion of pigment present is preferably from 0.5 to 15% by weight, more preferably from 1 to 10% by weight, based on the total weight of the ink.

The inkjet ink used in the method of the present invention preferably dries primarily by curing, i.e. by the polymerisation of the monomers present, as discussed hereinabove, and hence is a curable ink. The ink does not, therefore, require the presence of water or a volatile organic solvent to effect drying of the ink. Accordingly, the inkjet ink is preferably substantially free of water and volatile organic solvents. Preferably, the inkjet ink comprises less than 5 wt % of water and volatile organic solvent combined, preferably less than 3% by weight combined, more preferably, less than 2% by weight combined and most preferably less than 1% by weight combined, based on the total weight of the ink. Some water will typically be absorbed by the ink from the air and solvents may be present as impurities in the components of the inks, but such low levels are tolerated.

Other components of types known in the art may be present in the ink to improve the properties or performance. These components may be, for example, surfactants, defoamers, dispersants, synergists for the photoinitiator, stabilisers against deterioration by heat or light, reodorants, flow or slip aids, biocides and identifying tracers. The surfactant assists with wetting of the substrate surface by the ink, but it can be detrimental to the bonding process and so is preferably present at no more than 0.5% by weight, based on the total weight of the ink.

The inks of the invention may be prepared by known methods such as, for example, stirring with a high-speed water-cooled stirrer, or milling on a horizontal bead-mill.

The ink of the present invention is suitable for application by inkjet printing. The ink exhibits a desirable low viscosity, less than 100 mPas, preferably 50 mPas or less and most preferably 30 mPas or less at 25° C. The ink most preferably has a viscosity of 20 to 30 mPas at 25° C. Viscosity may be measured using a digital Brookfield viscometer fitted with a thermostatically controlled cup and spindle arrangement, such as model LDV1+.

Accordingly, the present invention also provides a method of inkjet printing, comprising jetting the ink as defined herein onto a substrate and curing the ink.

Substrates include those composed of polyvinyl chloride (PVC), polyester, polyethylene terephthalate (PET), polyethylene terephthalate glycol modified (PETG) and polyolefin (e.g. polyethylene, polypropylene or mixtures or copolymers thereof). In a preferred embodiment, the ink contains a chlorinated polyolefin resin and the ink is printed onto a polyolefin substrate. More preferably, the resin is a chlorinated version of the polyolefin material of the substrate. Most preferably, the resin is a chlorinated polypropylene and the substrate is polypropylene. When discussing the substrate, it is the surface which is most important, since it is the surface which is wetted by the ink. Thus, at least the surface of substrate is composed of the above-discussed material.

The ink of the present invention is cured by exposure to actinic radiation. The source of actinic radiation can be any source of actinic radiation that is suitable for curing radiation-curable inks but is preferably a UV source. Suitable UV sources include mercury discharge lamps, fluorescent tubes, light emitting diodes (LEDs), flash lamps and combinations thereof. One or more mercury discharge lamps, fluorescent tubes, or flash lamps may be used as the radiation source. When LEDs are used, these are preferably provided as an array of multiple LEDs.

The invention will now be described with reference to the following examples, which are not intended to be limiting.

EXAMPLES

Example 1

Two inks were prepared. The inks had formulations as shown in Table 1.

TABLE 1

| Ink formulations | | |
| --- | --- | --- |
| Component | Ink 1, wt % | Ink 2, wt % |
| IBOA | 18 | 18 |
| MEDA | 21.88 | 21.88 |
| NVC | 16.5 | 16.5 |
| DDDA | 20 | 20 |
| UV12 | 0.2 | 0.2 |
| CP343-1 | 2 | 0 |
| CN964A85 | 0 | 2 |
| EPD | 0.85 | 0.85 |
| ITX | 0.8 | 0.8 |
| BP | 2.88 | 2.88 |
| Irgacure 184 | 1.88 | 1.88 |
| TPO | 8.01 | 8.01 |

TABLE 1-continued

| Ink formulations | | |
| --- | --- | --- |
| Component | Ink 1, wt % | Ink 2, wt % |
| Cyan pigment dispersion | 6 | 6 |
| Byk 307 | 1 | 1 |
| Total | 100 | 100 |

IBOA, MEDA, NVC and DDDA are monomers, as defined herein. UV12 is a stabiliser. CP343-1 is a chlorinated polyolefin. CN964A85 is a urethane acrylate oligomer. EPD, ITX, BP, Irgacure 184 and TPO are photoinitiators. The cyan pigment dispersion contains PEA (59.0 wt %), UV12 (1.0 wt %), Solsperse 32000 (10.0 wt %), Heliogen blue (30.0 wt %). BYK307 is a surfactant.

The inks were prepared by first weighing the monomers into a suitable mixing vessel, placing the vessel under the mixing head of a Silverson stirrer and starting the stirrer. The polyolefin was added, were required, and the mixture stirred until all the polymer particles had dispersed. The temperature was monitored throughout to ensure that the temperature did not exceed 60° C. The remaining components were added to the mixture and the mixture stirred for a further five minutes.

Example 2

Each of the above ink formulations was coated on to a range of substrates using a K 2 applicator bar (12 μm wet film). The resulting films were cured using a standard mercury arc lamp supplied by Jenton, full power 25 m/min×2 passes (approximately 2,700 mW/cm$^2$ and total dose of 764 mJ/cm$^2$.

Adhesion of the inks to the substrates were measured by assessing scratch resistance and using a cross hatch tape removal test. The test is as follows. Score surface with an elcometer/blade to form a cross hatch area and apply scotch 3m610 tape across the scored area. After applying pressure, remove the tape and assess for ink removal from the substrate. A good result would typically have no more than 15% of the ink removed by the tape from the substrate. The results are set out in Table 2.

TABLE 2

| Ink adhesion. | | |
| --- | --- | --- |
| Substrate | Adhesion, ink 1 | Adhesion, ink 2 |
| Polycarbonate | Good | Good |
| PETG | Good | Good |
| Polystyrene | Good | Good |
| Fluted polypropylene | Good | Poor |

Example 3

One ink containing MEDA was prepared, along with a comparative ink containing THFA in place of MEDA, as in Example 1. The inks had formulations as shown in Table 3.

TABLE 3

Ink formulations

| Component | Ink 3, wt % | Comparative ink 1, wt % |
|---|---|---|
| IBOA | 12 | 12 |
| MEDA | 34.9 | 0 |
| THFA | 0 | 34.9 |
| NVC | 24 | 24 |
| UV12 | 0.4 | 0.4 |
| Photomer 6210 | 10.5 | 10.5 |
| ITX | 4.0 | 4.0 |
| BAPO | 2.8 | 2.8 |
| TPO | 2.8 | 2.8 |
| Cyan pigment dispersion | 8.6 | 8.6 |
| Total | 100 | 100 |

IBOA, MEDA, THFA and NVC are monomers, as defined herein. UV12 is a stabiliser. Photomer 6210 is an aliphatic urethane diacrylate oligomer. ITX, BAPO and TPO are photoinitiators. The cyan pigment dispersion contains PEA (59.0 wt %), UV12 (1.0 wt %), Solsperse 32000 (10.0 wt %), Heliogen blue (30.0 wt %).

Example 4

Each of the above ink formulations was coated on to a range of substrates using a K 2 applicator bar (12 μm wet film). The resulting films were cured using a standard mercury arc lamp supplied by Jenton, full power 25 m/min×2 passes (approximately 2,700 mW/cm$^2$ and total dose of 764 mJ/cm$^2$).

Adhesion of the inks to the substrates was measured by measuring the % area of ink removed using Scotch 3M 600 tape according to the ISO Standard Method BS EN ISO 2409 as described in Example 2. The results are set out in Table 4.

TABLE 4

Ink adhesion.

| Substrate | Adhesion, ink 3 | Adhesion, comparative ink 1 |
|---|---|---|
| PVC banner | Good | Good |
| Semi-rigid PVC | Good | Good |
| Self-adhesive vinyl | Good | Good |
| Polyester | Good | Poor |

Therefore THFA, which has good adhesion to these substrates, can be replaced by MEDA with no loss in adhesion performance. In fact, adhesion to polyester is better for the ink of the invention containing MEDA than the comparative ink containing THFA.

Example 5

Four inks were prepared, one of the invention (ink 4) and three comparative inks (comp. inks 2-4), as in Example 1. The inks had formulations as shown in Table 5.

TABLE 5

Ink formulations

| Component | Ink 4, wt % | Comp. ink 2, wt % | Comp. ink 3, wt % | Comp. ink 4, wt % |
|---|---|---|---|---|
| IBOA | 12 | 12 | 12 | 12 |
| NVC | 24 | 24 | 24 | 24 |
| MEDA | 35.1 | 0 | 0 | 0 |
| PEA | 0 | 34.9 | 35.1 | 0 |
| THFA | 0 | 0 | 0 | 35.1 |
| Photomer 6210 | 9.5 | 10.5 | 9.5 | 9.5 |
| UV12 | 0.4 | 0.4 | 0.4 | 0.4 |
| Cyan pigment dispersion | 0 | 8.6 | 0 | 0 |
| Black pigment dispersion | 6.5 | 0 | 6.5 | 6.5 |
| Darocur TPO | 8.5 | 2.8 | 8.5 | 8.5 |
| Irgacure 819 | 0 | 2.8 | 0 | 0 |
| ITX | 4 | 4 | 4 | 4 |
| Total | 100 | 100 | 100 | 100 |

IBOA, NVC, MEDA, PEA and THFA are monomers, as defined herein. Photomer 6210 is an aliphatic urethane diacrylate oligomer. UV12 is a stabiliser. Darocur TPO, Irgacure 819 and ITX are photoinitiators. The cyan pigment dispersion contains PEA (59.0 wt %), UV12 (1.0 wt %), Solsperse 32000 (10.0 wt %), Heliogen blue (30.0 wt %). The black pigment dispersion contains PEA (46.5 wt %), UV12 (1.5 wt %), Efka 7731 (12.0 wt %) and carbon black (40.0 wt %). Efka 7731 is a high molecular weight dispersant.

Example 6

Inks 3 and 4 and comparative inks 1-4 were printed onto a Banner PVC substrate and cured using a Mimaki UJF3042 benchtop printer, in 8-pass mode, equipped with a 385 nm UV-LED lamp (500 mW/cm$^2$ output and total dose of 120 mJ/cm$^2$).

Adhesion of the inks to the substrates was measured by measuring the % area of ink removed using Scotch 3M 600 tape according to the ISO Standard Method BS EN ISO 2409 as described in Example 2. The results are set out in Table 6.

TABLE 6

Ink adhesion

| | Ink 3, wt % | Ink 4, wt % | Comp. ink 1, wt % | Comp. ink 2, wt % | Comp. ink 3, wt % | Comp. ink 4, wt % |
|---|---|---|---|---|---|---|
| % ink removed | 0 | 0 | 0 | 11 | 30 | 0 |

As can be seen from Table 6, inks 3 and 4 containing MEDA perform equally to comparative inks 1 and 4 containing THFA—all of the ink remains intact, showing that MEDA is a good substitute for THFA. In contrast, comparative inks 2 and 3 containing PEA, are less adhesive than comparative inks 1 and 4 containing THFA, showing that PEA is not a good substitute for THFA.

What is claimed is:

1. An inkjet ink comprising: one or more monofunctional (meth)acrylate monomers, including 2-methyl-2-ethyl-1,3-dioxolane-4-yl)methyl acrylate (MEDA); a pigment; a photoinitiator; and N-vinyl caprolactam.

2. An inkjet ink as claimed in claim 1, wherein the ink comprises at least two monofunctional (meth)acrylate monomers, including MEDA.

3. An inkjet ink as claimed in claim 1, wherein the ink further comprises at least two N-vinyl amide monomers and/or N-(meth)acryloyl amine.

4. An inkjet ink as claimed in claim 1, wherein the ink further comprises one or more di- and/or multifunctional monomers.

5. An inkjet ink as claimed in claim 1, wherein the MEDA is present at 10-45% by weight, based on the total weight of the ink.

6. An inkjet ink as claimed in claim 1, wherein the ink comprises MEDA, isobornyl acrylate (IBOA) and N-vinyl caprolactam (NVC).

7. An inkjet ink as claimed in claim 1, wherein the ink is substantially free of tetrahydrofurfuryl acrylate (THFA).

8. An inkjet ink as claimed in claim 1, wherein the ink further comprises a radiation-curable oligomer.

9. An inkjet ink as claimed in claim 1, wherein the ink further comprises a resin.

10. An inkjet ink as claimed in claim 9, wherein the resin is a chlorinated polyolefin.

11. An inkjet ink as claimed in claim 9, wherein the resin is present at 0.1-5% by weight, based on the total weight of the ink.

12. An inkjet ink as claimed in claim 9, wherein the ink is substantially free of water and volatile organic solvent.

13. A method of inkjet printing, comprising jetting the ink as claimed in claim 9 onto a substrate and curing the ink.

14. A method as claimed in claim 13, wherein the ink contains a chlorinated polyolefin resin and the substrate is composed of polyolefin.

15. A method as claimed in claim 14, wherein the substrate is composed of polypropylene.

\* \* \* \* \*